United States Patent [19]
Stomp et al.

[11] Patent Number: 5,122,466
[45] Date of Patent: Jun. 16, 1992

[54] BALLISTIC TRANSFORMATION OF CONIFERS

[75] Inventors: Anne-Marie Stomp; Arthur K. Weissinger; Ronald R. Sederoff, all of Raleigh, N.C.

[73] Assignee: North Carolina State University, Raleigh, N.C.

[21] Appl. No.: 365,428

[22] Filed: Jun. 13, 1989

[51] Int. Cl.$^5$ .............. C12N 15/00; C12N 5/00; C12P 21/00; C12P 21/04
[52] U.S. Cl. .............. 435/172.3; 435/69.1; 435/70.1; 435/240.45; 435/240.49; 435/320.1; 935/52; 935/56; 935/67
[58] Field of Search .............. 435/70.1, 172.3, 320, 435/69.1, 320.1, 240.45, 240.49; 935/52, 56, 67; 800/205, DIG. 51, DIG. 49

[56] References Cited

U.S. PATENT DOCUMENTS 4,417,417  11/1983  Mehra-Palta ................ 47/58
4,795,855  6/1989   Fillatti et al. ................ 800/1
4,945,050  7/1990   Sandford et al. ........... 435/172.1

FOREIGN PATENT DOCUMENTS 0270356  8/1968  European Pat. Off. .
0301749  1/1989  European Pat. Off. .

OTHER PUBLICATIONS

Klein et al., 1987, Nature 327: 70-73.
Klein et al., 1988, Bio/Technology 6(5): 559-563.
Kaul, K., 1987, Plant Cell Reports, 5: 5-7.
Kaul et al., 1985, Plant Cell Reports, 4: 180-183.
M. Chapel and K. Glimelius, *Plant Cell Reports*, 9, 105-108 (1990).
W. Gordon-Kamm et al., *The Plant Cell 2*, 603-618 (Jul. 1990).
Johnston, S. A. et al., *Science 240*, 1538 (1988).
Klein, T. M. et al., *Proc. Natl. Acad. Sci. USA 85*, 8502 (1988).
Mott, R. L. and Amerson, H. V., *Tech. Bul.*, No. 271, 2 (1981).
Amerson, H. V. et al., in *Genetic Manipulation of Woody Plants*, 117 (J. Hanover and D. Keathey eds., 1987).
Boynton, J. E. et al., *Science 240*, 1534 (1988).
Jefferson, R. A. et al., *The EMBO Journal 6*, No. 13, 3901 (1987).

*Primary Examiner*—David T. Fox
*Attorney, Agent, or Firm*—Bell, Seltzer, Park & Gibson

[57] ABSTRACT

A method of transforming conifers with a DNA construct comprising an expression cassette is disclosed herein. The method comprises the steps of (a) providing a plant tissue target, the plant tissue target comprised of conifer tissue, the cells of the conifer tissue including cell walls; and then (b) propelling the DNA construct at the plant tissue target at a velocity sufficient to pierce the cell walls and deposit the DNA construct within a cell of the tissue target to thereby provide a transformed plant tissue. Preferably, shoots are then induced to form on the transformed plant tissue. Preferred plants for carrying out the present invention are the members of the genus Pinus.

25 Claims, 3 Drawing Sheets

BALLISTIC TRANSFORMATION OF CONIFERS

BACKGROUND OF THE INVENTION

Conifers in general, and pines in particular, are extremely important crop plants. This group of trees supplies fiber and wood to a large fraction of the world's population. Genetic improvement in pines has been limited by the long generation times of these plants, and the most advanced breeding programs have carried out no more than about three generations of selection. Genetic improvement by gene transfer methods has great potential application in this area, but methods for the introduction of foreign DNA and the subsequent production of transgenic plants, although available for many crop species, have been difficult to provide for the conifers.

Techniques have been developed for transforming conifers with *Agrobacterium tumefaciens* vectors. See, e.g., Sederoff, Stomp, Chilton, and Moore, Gene Transfer into Loblolly Pine by *Agrobacterium tumefaciens*, 4 Bio/Technology 647 (1986); see also U.S. Pat. No. 4,459,355 to Cello and Olsen. Such systems add complexity to methods for the genetic modification of plants because they add a second living system (the Agrobacterium species) to the method. More recently, in other plants, considerable interest has focused on the use of ballistic microprojectiles as DNA vectors for the transformation of plant cells. See, e.g., McCabe et al., *Stable Transformation of Soybean (Glycine Max) by Particle Acceleration*, 6 Bio/Technology 923 (1988); Klein et al., *Transfer of Foreign Genes into Intact Maize Cells with High-Velocity Microprojectiles*, 85 Proc. Natl. Acad. Sci. USA 4305 (1988). While these ballistic transformation methods appear attractive, it has not previously been suggested how they might be applied to the transformation of conifers.

The following problems in developing genetic engineering procedures for plants have been noted: First, unlike unicellular microorganisms, plant cells have a low rate of proliferation. Second, plant cells are much more sensitive to their environment in relation to viability, proliferation and regeneration to plants. Third, in order to establish whether a foreign gene has been usefully integrated into a plant cell, it is necessary to establish that the regenerated plant expresses the phenotype. Fourth, plant cells have rigid cell walls. See U.S. Pat. No. 4,795,855 to Fillatti and Comai, at Col. 1. In addition, when plant tissue is wounded during a transformation process, it can be difficult to obtain subsequent morphogenesis from the wounded, transformed tissue. Untransformed tissue within the treated tissue sample may undergo morphogenesis, but this is not the object of the transformation process.

Accordingly, an object of the present invention is to provide a method for transforming conifers with microprojectiles.

Another object of the present invention is to provide a method of transforming plant tissue in which the tissue transformed is capable of subsequently undergoing morphogenesis.

Another object of the present invention is to provide a method of transforming conifers which yields stable transformation.

SUMMARY OF THE INVENTION

A method of transforming conifers With a DNA construct comprising an expression cassette, which construct comprises, in the 5' to 3' direction, a transcription initiation region and a region which codes for a peptide positioned downstream from said transcription initiation region and under the transcriptional regulation thereof, is disclosed herein. The method comprises the steps of (a) providing a plant tissue target, the plant tissue target comprised of conifer tissue, the cells of the conifer tissue including cell walls; and then (b) propelling the DNA construct at the plant tissue target at a velocity sufficient to pierce the cell walls and deposit the DNA construct within a cell of the tissue target to thereby provide a transformed plant tissue. Preferably, the DNA construct is carried by a microprojectile, and is propelled at the plant tissue target by propelling the microprojectile at the plant tissue target.

A preferred embodiment of the present invention is a method of transforming conifers with a DNA construct as described above, the method comprising the steps of (a) providing a plant tissue target, the plant tissue target selected from the class consisting of Pinus meristematic tissue and Pinus tissue capable of induction into meristematic tissue, the cells of the tissue target including cell walls; (b) propelling the DNA construct at the plant tissue target at a velocity sufficient to pierce the cell walls and deposit the DNA construct within a cell of the tissue target to thereby provide a transformed plant tissue; and then (c) generating shoots from the transformed plant tissue. Preferably, the DNA construct is carried by a microprojectile, and is propelled at the plant tissue target by propelling the microprojectile at the plant tissue target.

The methods disclosed herein can be used to produce a transformed conifer plant comprising transformed conifer cells, the transformed conifer cells containing a heterologous DNA construct comprising an expression cassette, which construct comprises, in the 5' to 3' direction, a transcription initiation region and a region which codes for a peptide positioned downstream from the transcription initiation region and under the transcriptional regulation thereof, wherein the expression cassette is subject to the proviso that T-DNA borders are excluded therefrom. Such transformed conifers cannot be produced through the use of an Agrobacterium transformation procedure. T-DNA borders may optionally be included on the expression cassette employed in practicing the method of the present invention, and plants produced by this method, with the resulting plant product containing T-DNA borders on the expression cassette like plants produced by an Agrobacterium transformation procedure.

DETAILED DESCRIPTION OF THE INVENTION

The term "conifer," as used herein, refers to a member of the order Coniferae in the sub-phylum Gymnospermae in the phylum Spermaphyta. Exemplary conifers which may be used in practicing the present invention are the members of the family Pinaceae, which include, for example, loblolly pine (*Pinus taeda*), slash pine (*Pinus elliotii*), longleaf pine (*Pinus palustris*), shortleaf pine (*Pinus echinata*), ponderosa pine (*Pinus ponderosa*), red pine (*Pinus resinosa*), jack pine (*Pinus banksiana*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*), and Virginia pine (*Pinus virginiana*); Douglas-fir (*Pseudotsuga menziesii*); Western hemlock (*Tsuga canadensis*); Sitka spruce (*Picea glauca*); redwood (*Sequoia sempervirens*); the true firs including silver fir (*Abies amabilis*), grand fir (*Abies grandis*) noble fir (*Abies procera*), white fir (*Abies concolor*), balsam fir (*Abies balsamea*); and the cedars which include Western red cedar (*Thuja plicata*), incense cedar (*Libocedrus decurrens*), Port Orford cedar (*Chamaecyparis lawsoniona*), and Alaska yellow-cedar (*Chamaecyparis nootkatensis*); and Western larch (*Laryx occidentalis*). Preferred for practicing the present invention are the pines (genus Pinus), and most preferred for practicing the present invention is the loblolly pine (*Pinus taeda*).

The DNA construct employed in the present invention includes transcriptional and translational initiation regions and, optionally, transcriptional and translational termination regions, with the initiation regions 5' to the gene of interest and the termination regions 3' to the gene of interest. All of these regulatory regions should be capable of operating in the cells of the tissue to be transformed, either in a constitutive or a tissue-specific manner.

The transcriptional initiation region, which preferably includes the RNA polymerase binding site (promoter), may be native to the host conifer to be transformed or may be derived from an alternative source, where the region is functional in the host. Other sources include the Acrobacterium T-DNA genes, such as the transcriptional initiation regions for the biosynthesis of nopaline, octopine, mannopine, or other opine transcriptional initiation regions, transcriptional initiation regions from plants or woody species other than the host species, transcriptional initiation regions from viruses (including host specific viruses), or partially or wholly synthetic transcription initiation regions. Transcriptional initiation and termination regions are described by deGreve, J. Mol. Appl. Genet. (1983) 1:499-511; Salomon et al., EMBO J. (1984) 3:141-146; Velten et al., ibid. (1984) 3:2723-2730; Garfinkel et al., Cell (1983) 27:143-153: and Barker et al., Plant Mol. Bio. (1983) 2:335-350.

The transcriptional initiation regions may not only include the RNA polymerase binding site, but may also include regions which regulate transcription, where the regulation involves, for example, chemical or physical repression or induction (e.g., regulation based on metabolites or light), or regulation based on cell differentiation, such as associated with leaves, roots, seed, or the like. Thus, the transcriptional initiation region, or the regulatory portion of such region, is obtained from an appropriate gene which is regulated, for example, the 1,5-ribulose biphosphate carboxylase gene, which is light-induced and used for transcriptional initiation, stress-induced genes, heat shock genes which are temperature regulated, wound induced genes, meristem specific genes, etc.

The 3' termination region may be derived from the same gene as the transcriptional initiation region or a different gene. For example, where the gene of interest has a transcriptional termination region functional in the woody species, that region may be retained with the gene. An expression cassette can be constructed which will include the transcriptional initiation region, the gene of interest under the transcriptional regulational control of the transcriptional initiation region, the initiation codon, the coding sequence of the gene, with or without introns, the translational stop codons, followed by the transcriptional termination region, which will include the terminator, and may include a polyadenylation signal sequence and other sequences associated with transcriptional termination. The direction is 5'-3' in the direction of transcription. The cassette will usually be of a length less than about 10 kilobases (kb), frequently less than about 6 kb, usually being at least about 1 kb, more usually being at least about 2 kb.

The gene of interest may be derived from a chromosomal gene, cDNA, a synthetic gene, or combinations thereof. Where the expression product of the gene is to be located in a cellular compartment other than the cytoplasm, the gene will usually be constructed to include particular amino acid sequences which result in translocation of the product to a particular site, which may be an organelle, such as the chloroplast, mitochondrion or nucleus, the cell plasma membrane, or may be secreted into the periplasmic space or into the external environment of the cell. Various secretory leaders, membrane integrator sequences, and translocation sequences for directing the peptide expression product to a particular site are described in the literature. See, for example, Cashmore et al., Biotechnology (1985) 3:803-808, Wickner and Lodish, Science (1985) 230:400-407.

Genes of interest for use in conifers include a wide variety of phenotypic and non-phenotypic properties. Among the phenotypic properties are enzymes which provide for resistance to stress, such as dehydration resulting from heat and salinity, herbicides, toxic metal or trace elements, or the like. Resistance may be as a result of a change in the target site, enhancement of the amount of the target protein in the host cell, the increase in one or more enzymes involved with the biosynthetic pathway to a product which protects the host against the stress, and the like. Genes may be obtained from prokaryotes or eukaryotes, bacteria, fungi, e.g., yeast, viruses, plants, mammals or be synthesized in whole or in part. Illustrative genes include glyphosphate resistant 3-enolpyruvylphosphoshikinate synthase gene, nitrilase, genes in the proline and glutamine biosynthetic pathway, metallothioneins, etc. Other genes of interest may be involved with regulation of growth, such as manipulations of source/sink (carbon partitioning) relations, apical dominance, photosynthetic efficiency, such as altering the efficiency of RuBP carboxylase, or changing the quality of the woods, such as altering lignin to cellulose ratios or the length or diameter of wood fibers.

One or more cassettes may be involved, where the cassettes may be employed in tandem for the expression of independent genes which may express products independently of each other or may be regulated concurrently, where the products may act independently or in conjunction. When multiple cassettes are employed, they may be on the same plasmid or on different plasmids. When the cassettes are on different plasmids, these plasmids may both be carried by the same microprojectile, or they may be carried on different microprojectiles and these microprojectiles mixed together and propelled at the tissue target.

The expression cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the conifer host. The markers may be protection against a biocide, such as antibiotics, toxins, heavy metals, or the like; provide complementation, by imparting prototrophy to an auxotrophic host; or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase, providing indigo production, luciferase, providing visible light production, NPTII, providing kanamycin resistance or G418 resistance, HPT, providing hygromycin resistance, and the mutated aroA gene, providing glyphosate resistance. The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Maniatis et al., Molecular Cloning: A Laboratory Manual, Cold Spring Harbor Laboratory, Cold Spring Harbor, N.Y., 1982.

Any ballistic cell transformation apparatus can be used in practicing the present invention. Exemplary apparatus is disclosed in Sanford et al., *Delivery of Substances into Cells and Tissues using a Particle Bombardment Process*, 5 Particulate Science and Technology 27 (1988), in Klein et al., *High-velocity Microprojectiles for Delivering Nucleic Acids into Living Cells*, 327 Nature 70 (1987), and in Agracetus European Patent Application Publication No. 0 270 356, titled *Pollen-mediated Plant Transformation*. Such apparatus has been used to transform maize cells, Klein et al., 85 Proc. Natl. Acad. Sci. USA 4305 (1988), soybean callus, Christou et al., 87 Plant Physiol. 671 (1988); McCabe et al., 6 Bio/Technology 923 (1988), yeast mitochondria, Johnston et al., 240 Science 1538 (1988), and Chlamydomonas chloroplasts, Boynton et al., 240 Science 1534 (1988).

We used a commercially available device from Biolistics, Inc., 108 Langmuir Laboratory, Cornell Business and Technology Park, Brown Road, Ithaca, N.Y. 14850 (telephone no. 607-257-6056). This device is designated a Model BPG-4 Particle Acceleration Apparatus and is configured essentially as described in Klein et al., 327 Nature 70 (1987). The device comprises a bombardment chamber which is divided into two separate compartments by an adjustable-height stopping plate. An acceleration tube is mounted on top of the bombardment chamber. A macroprojectile is propelled down the acceleration tube at the stopping plate by a gunpowder charge. The stopping plate has a bore hole formed therein which is smaller in diameter than the macroprojectile, the macroprojectile carries the microprojectile(s), and the macroprojectile is aimed and fired at the bore hole. When the macroprojectile is stopped by the stopping plate, the microprojectile(s) are propelled through the bore hole. The target tissue is positioned in the bombardment chamber so that microprojectiles propelled through the bore hole penetrate the cell walls of the cells in the target tissue and deposit DNA constructs carried thereon in the cells of the target tissue.

The bombardment chamber is partially evacuated prior to use to prevent atmospheric drag from unduly slowing the microprojectiles. The chamber is only partially evacuated so that the target tissue is not dessicated during bombardment thereof. A vacuum of between about 400 to about 800 millimeters of mercury is suitable.

It is not clear that the microprojectile is a critical element of this apparatus and method. For example, an aqueous solution containing the DNA construct as a precipitate could be carried by the macroprojectile (e.g., by placing the aqueous solution directly on the plate-contact end of the macroprojectile without a microprojectile, where it is held by surface tension), and the solution alone propelled at the plant tissue target (e.g., by propelling the macroprojectile down the acceleration tube in the same manner as described above). Other approaches include placing the DNA precipitate itself ("wet" precipitate) or a freeze-dried DNA precipitate directly on the plate-contact end of the macroprojectile without a microprojectile. In the absence of a microprojectile, it is believed that the DNA construct must either be propelled at the tissue target at a greater velocity than it would need be if carried by a microprojectile, or the DNA construct caused to travel a shorter distance to the target tissue (or both). A ballistic transformation technique carried out without a microprojectile is applicable to plants in general and not limited to conifers, though conifers are currently preferred and pines are currently more preferred. In overview, this is a method of transforming plants with a DNA construct comprising an expression cassette, which construct comprises, in the 5' to 3' direction, a transcription initiation region and a region which codes for a peptide positioned downstream from said transcription initiation region and under the transcriptional regulation thereof, the method comprising the steps of (a) providing a plant tissue target, the cells of the plant tissue target including cell walls, (b) providing an aqueous solution containing said DNA construct; and (c) propelling the aqueous solution at the plant tissue target at a velocity sufficient to pierce the cell walls and deposit the DNA construct within a cell of the tissue target. As noted above, the technique could be carried out with the DNA construct as a DNA precipitate (wet or freeze-dried) alone, in place of the aqueous solution containing the DNA construct.

It is currently preferred to carry the DNA construct on a microprojectile. The microprojectile may be formed from any material having sufficient density and cohesiveness to be propelled through the cell wall, given the particle's velocity and the distance the particle must travel. Non-limiting examples of materials for making microprojectiles include metal, glass, silica, ice, polyethylene, polypropylene, polycarbonate, and carbon compounds (e.g., graphite, diamond). Metallic particles are currently preferred. Non-limiting examples of suitable metals include tungsten, gold, and iridium. The particles should be of a size sufficiently small to avoid excessive disruption of the cells they contact in the target tissue, and sufficiently large to provide the inertia required to penetrate to the cell of interest in the target tissue. Particles ranging in diameter from about one-half micrometer to about three micrometers are suitable. Particles need not be spherical, as surface irregularities on the particles may enhance their DNA carrying capacity.

The DNA construct may be immobilized on the particle by precipitation. The precise precipitation parameters employed will vary depending upon factors such as the particle acceleration procedure employed, as is known in the art. The carrier particles may optionally be coated with an encapsulating agent such as polylysine to improve the stability of DNA constructs immobilized thereon, as discussed in EPO Application 0 270 356, at Column 8.

Any target tissue capable of subsequent clonal propagation, whether by organogenesis or embryogenesis, may be employed in practicing the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include pollen, embryos, cotyledons, hypocotyls, megagametophytes, callus tissue, stems, needles, needle fascicles, existing meristematic tissue (e.g., apical meristems, axillary buds, and root meristems), and induced meristem tissue (e.g., cotyledon meristem and hypocotyl meristem). Preferred is tissue selected from the class consisting of meristematic tissue (both existing and induced) and tissue capable of induction into meristematic tissue. More preferred, as discussed below, is cotyledon and hypocotyl tissue, with cotyledon tissue most preferred. Target tissue is oriented for bombardment so that the microprojectile(s) enter one or more of the cells to be transformed.

Exemplary methods of inducing meristem formation in conifer callus tissue are disclosed in Gladfelter and Phillips, *De novo Shoot Organogenesis of Pinus eldarica Medw. in vitro*, 6 Plant Cell Reports 163 (1987), in Ball, *Differentiation in a Callus Culture of Sequoia sempervirens*, 14 Growth 295 (1950), and in Simola and Honkanen, *Organogenesis and Fine Structure in Megagametophyte Callus Clones of Picea abies*, 59 Physiol. Plant 551 (1983). Additional methods of inducing differentiation in conifer tissue are disclosed in Winton and Verhagen, *Shoots from Douglas-fir Cultures*, 55 Can. J. Bot. 1246 (1977), in Kaul, *Plant regeneration from cotyledon-hypocotyl Explants of Pinus strobus L.*, 6 Plant Cell Reports 5 (1987), in Mott and Amerson, *A Tissue Culture Process for the Clonal Production of Loblolly Pine Plantlets*, Tech. Bul. No. 271 of the North Carolina Agricultural Research Service (1981)(hereinafter "Mott and Amerson"), in U.S. Pat. No. 4,417,417 to Mehra-Palta, titled *Clonal Propagation of Gymnosperms* (the disclosure of which is to be incorporated herein by reference) (hereinafter "the '417 patent"), and in Aitken-Christie et al., *Multiplication of Meristematic Tissue—A New Tissue Culture System for Radiata Pine*, in Genetic Manipulation of Woody Plants, 413 (J. Hanover and D. Keathley eds. 1987).

A preferred clonal propagation method for practicing the present invention is the method originally described by Mott and Amerson, and, subsequently, more broadly described in the '417 patent. This method is particularly preferred where the species to be transformed is selected from the genus Pinus, and is the most preferred method when the species to be transformed is *Pinus taeda*. The method is preferably practiced with cotyledon tissue or hypocotyl tissue, with cotyledon tissue most preferred because the large flat surface of the cotyledon provides an ideal target for the propelled DNA constructs when the cotyledon is oriented substantially at a right angle to the path thereof. This method comprises, in overview, the steps of (a) treating excised cotyledon or hypocotyl tissue on a shoot induction medium (e.g., a cytokinin containing medium) for a time sufficient to induce formation of adventitious buds on the tissue, then (b) transferring the treated tissue to a nutrient medium free of exogenous growth factors until the induced adventitious buds produce rootable shoots, then (c) treating the rootable shoots on a root induction medium for a time sufficient to induce formation of adventitious roots, and then (d) transferring the treated shoots to a nutrient medium free of exogenous growth factors until the roots elongate. Numerous different shoot and root induction media suitable for use in this procedure are known. This method results in the production of propagules which may be transferred to and raised in soil to form adult plants.

The clonal propagation system described immediately above provides developmental windows during which the tissue is most suitable for transformation by DNA bombardment. As practiced in conjunction with the present invention, the tissue is preferably bombarded with the DNA construct after the tissue has been treated on a shoot induction medium for a time at least sufficient to induce the subsequent formation of meristematic tissue on the target tissue. Also, the tissue is preferably bombarded with the DNA construct before it is transferred to a growth medium for the production of rootable shoots. More preferably, the tissue is raised on shoot induction medium for a time sufficient to induce the formation of superficial meristematic tissue from periclinal divisions of at least the first and second sub-epidermal cell layers, then bombarded with the DNA construct before it is transferred to a growth medium for the production of rootable shoots. Most preferably, the tissue is raised on shoot induction medium for a time sufficient to induce the formation of superficial meristematic tissue from periclinal divisions of at least the first and second sub-epidermal cell layers, then bombarded with the DNA construct before adventitious buds have developed on the target tissue, and then returned to a shoot induction medium for a time sufficient to induce the formation of adventitious buds. The development of propagules and plants is then carried out as described above.

We hypothesize that these developmental windows correspond to periods in the propagation of the tissue during which greater numbers of cells in the tissue being bombarded are in a specific phase of their cell cycle when they are more amenable to integration or expression of foreign DNA. Thus, the greater the proportion of cells in this phase in the tissue being bombarded, the greater the probability of obtaining stable expression in the bombarded tissue.

In our hands, after *Pinus taeda* seed has been germinated for five days in hydrogen peroxide solution, the embryos therein sacrificed, and the tissue excised therefrom transferred to shoot induction medium, bombardment with the DNA constructs is preferably carried out between about days 2 and 9 after excision, and is more preferably carried out between about days 5 and 7 after excision.

In our hands, after *Pinus radiata* seed has been germinated for one day in hydrogen peroxide solution, the embryos therein sacrificed, and the tissue excised therefrom transferred to shoot induction medium, bombardment with the DNA constructs is preferably carried out on about day 2 after excision or later, and is more preferably carried out on about day 7 after excision or later.

The present invention is explained in greater detail in the following examples. These examples are provided for illustrative purposes only, and are not to be taken as restrictive of the present invention.

EXAMPLE 1

Preparation of Loblolly Pine Cotyledons For Bombardment

Cotyledons were prepared and cultured following the method of Mott and Amerson. Loblolly pine seeds were scarified with a razor blade at the micropylar end. Nicked seeds were soaked in 1% hydrogen peroxide, using 1 ml of peroxide solution per seed, at 30° C. under continuous light (cool white fluorescent), for 5 days with daily changes of peroxide. Seed coats were removed from seeds whose radicle had emerged 2–4 mm. Peeled seeds were then surface sterilized by soaking in 1% calcium hypochlorite, with a small amount of detergent as a wetting agent, for 10 minutes with occasional stirring. Seeds were rinsed 3 times with excess sterile water and transferred to a sterile petri dish for embryo excision and explant preparation.

Cotyledons were aseptically removed from the embryo axis and placed separately on shoot induction medium; a modified Murashige and Skoog, 15 *Physiologia Plantarum* 31 (1962), medium with 40 uM benzyladenine and 0.05 uM naphthaleneacetic acid (Table I).

TABLE 1

| Composition of Shoot Induction Medium[1] | |
|---|---|
| Component | Medium Concentration (mM) |
| $MgSO_4\ 7H_2O$ | 1.5 |
| $MnSO_4\ H_2O$ | 0.1 |
| $ZnSO_4\ H_2O$ | 0.03 |
| $CuSO_4\ 5H_2O$ | 0.0001 |

TABLE 1-continued

| Composition of Shoot Induction Medium[1] | |
|---|---|
| Component | Medium Concentration (mM) |
| $CaCl_2\ 2H_2O$ | 3.0 |
| KI | 0.005 |
| $CoCl_2\ 6H_2O$ | 0.001 |
| $KH_2PO_4$ | 1.25 |
| $H_3BO_3$ | 0.1 |
| $Na_2MoO_4\ 2H_2O$ | 0.001 |
| $FeSO_4\ 7H_2O$ | Fe 0.1 |
| $Na_2EDTA$ | Na 0.2 |
| $KNO_3$ | 1.0 |
| KCl | 9.0 |
| Glutamine | 10.0 |
| Benzyladenine(2) | 0.04 |
| Naphthaleneacetic acid(2) | 0.00005 |
| Thiamine HCl | 0.1 mg/l |
| Nicotinic Acid | 0.5 mg/l |
| Pyridoxin HCl | 0.1 mg/l |
| Myo-Inositol | 100.0 mg/l |
| Sucrose | 20.0 g/l |
| Agar(3) | 7.0 g/l |

[1]Medium is a modified Murashige and Skoog, 15 Physiologia Plantarum 31 (1962), medium, further modified by Brown and Lawrence, 14 Forest Science 62 (1968), and Mott and Amerson. Glutamine has been substituted for inorganic nitrogen.

This medium contains 10 mM glutamine and 1 mM $NO_3$ as the sources of nitrogen, additional $K^+$ is supplied by KCl at 9 mM, vitamins are those of Brown and Lawrence, 14 *Forest Science* 62 (1968), without asparagine, and the sucrose concentration is 2 g/liter. The medium is solidified with Gibco Phytoagar, commercial grade, and washed exhaustively with deionized water following the method of Redenbaugh (personal communication) as follows: (I) WASHING AGAR: fill a 600 ml beaker with unwashed agar, pour the agar into a 4 liter beaker, fill the beaker to 4 liters with deionized water while stirring, let the agar settle, pour off the wash water, and repeat these steps until the wash water is clear; (II) PRIMARY DRYING: stir water/agar mixture, pour the mixture into a pillow case, remove water and air from the agar by squeezing the pillow case by hand, remove the agar from the pillow case, and spread the agar on a sheet of foil to speed drying: (III) FINAL DRYING: place the agar in a warming oven for 2 to 4 days, depending on the temperature, until dry, and grind the agar in a blender to a fine powder. Seven g/liter of this washed agar has the same gelling strength as 1% Difco Bactoagar.

Phytohormone stock solutions were prepared by dissolving hormones at high concentration s (typically 100 mM or 10 mM) in dimethylsulfoxide (DMSO). Medium with phytohormones (DMSO not exceeding 0.05%) was autoclaved for 15 minutes at 121° C. Filter-sterilized glutamine was added to the cooled medium which was poured into 60×15 mm disposable petri dishes. Incubation of all plant material was at 23° C. with a 16 hr photoperiod under 25–45 uE/m² sec, using a Sylvania GroLux wide spectrum fluorescent light.

EXAMPLE 2

Preparation of DNA

Plasmid pBI 221.1 is a high copy number plasmid containing the bacterial gene for beta-glucuronidase under the control of the CaMV 35S promoter inserted into the polylinker of pUC19. See Jefferson et al., 6 *EMBO Journal* 3901 (1987). Plasmid DNA was prepared essentially as described by Birnboim (1983). DNA concentrations were determined by fluorimetry.

EXAMPLE 3

Preparation of Microprojectiles

Plasmid DNA was precipitated in the presence of microprojectiles essentially as described by Klein et al., 327 *Nature* 70 (1987). Microprojectiles were prepared from tungsten powder with a diameter of approximately 1.1 um (designated "M17" by Biolistics, Inc. . Each bombardment delivered approximately 150 ug of particles associated with 0.36 ug of plasmid DNA in a total slurry volume of 2.5 ul. DNA preparations used for microprojectile bombardments contained a mixture of supercoiled, open circle and linear molecules.

EXAMPLE 4

Microprojectile Bombardment Parameters

All bombardments were carried out with a Model BPG4 Particle Acceleration Apparatus (Biolistics, Inc., 108 Langmuir Lab, Cornell Business and Technology Park, Ithaca, N.Y. 14850) configured essentially as previously described (Klein et al., supra, 1987). Stopping plates and macroprojectiles were also supplied by Biolistics, Inc. Powder charges were .22 caliber number 1A2 (grey), purchased from ITT, Phillips Drill Division, Portland, Oreg. All bombardments were carried out at a pressure of 28" Hg, at a range of approximately 12 cm from the stopping plate to the surface of the treated tissue.

EXAMPLE 5

Tissue Culture After Bombardment

After bombardment, cotyledons were cultured on shoot induction medium. After 4 weeks on shoot induction medium, cotyledons were transferred to one-half strength Gresshof and Doy, 107 *Planta (Berl.)* 161 (1972), medium with 2% sucrose, 0.5% acid-washed charcoal (Sigma), 0.7% washed agar, and without phytohormones, to enhance shoot development. After one, 4-week subculture, cotyledons were transferred to one-half strength Gresshof and Doy medium without charcoal to continue shoot growth. Subsequent subcultures to fresh medium without charcoal were done at 4-week intervals. Growth chamber environmental conditions were identical to those used for shoot induction.

EXAMPLE 6

Assay of Bombarded Tissue for GUS Activity

Subsets of cotyledons were sampled at various times to determine the frequency of beta-glucuronidase (GUS) activity. Cotyledons were incubated in substrate solution, containing 2.0 mM 5-bromo-4-chloro-3-indoyl-beta-D-glucuronic acid (X-gluc), 0.1M $NaPO_4$ buffer, pH 7.0, 0.01M $Na_2EDTA$, pH 7.0, 0.5 mM $K_4Fe(CN)_6 3H_2O$, pH 7.0, and 0.5 mM $K_3Fe(CN)_6$ and 0.1% Triton X-100 (A. Montoya, personal communication), for 24 hours at 37° C. To score for GUS activity, cotyledons were individually scanned under a Wild stereo-microscope.

EXAMPLE 7

Histological Analysis of GUS Positive Tissue

Histological analysis of GUS positive material was carried out on paraffin embedded sections following the method developed by Elliot Meyerowitz, at the Division of Biology 156-29, California Institute of Technology, Pasadena, Calif. 91125. In brief, cotyledons were quick frozen in absolute ethanol/dry ice. Freeze-substitution was carried out at −70° C. for 1-2 days in a large excess of absolute ethanol. Cotyledons were then brought to room temperature by sequential incubations at −20° C. and 4° C.; each temperature shift lasting from several hours to overnight. After samples reached room temperature, the cotyledons were placed in fresh absolute ethanol. The tissue should sink at this step. Complete paraffin embedding is not possible if water remains in the tissue. Samples were then incubated in 2 changes of toluene for 15 minutes each, followed by a final third toluene incubation at 60° C. for 30 minutes. The samples were then transferred to paraffin (Tissue Prep) and incubated at 60° C. for 1 hour. Cotyledons were oriented and embeded in fresh paraffin and 12-15 um sections were cut. Sections were scanned for GUS positive cells on a Leitz Diaplan compound microscope using interference contrast and polarized light.

EXAMPLE 8

Determining the Effect of Time of Bombardment on GUS Expression in *Pinus taeda*

Cotyledons were removed from *Pinus taeda* embryos germinated for five days and placed on shoot induction medium, all as described in Example 1 above. Subsets of these cotyledons were bombarded, in accordance with the procedure described in Example 4 above, on day 2, day 5, day 7, and day 9 after removal of the cotyledon from its embryo and transfer to the shoot induction medium. Bombarded cotyledons were assayed for GUS activity 24 hours after bombardment (day 1), and on day 3, day 6, and day 8. These days are referred to as "stain days" in the figures.

Figure 1:
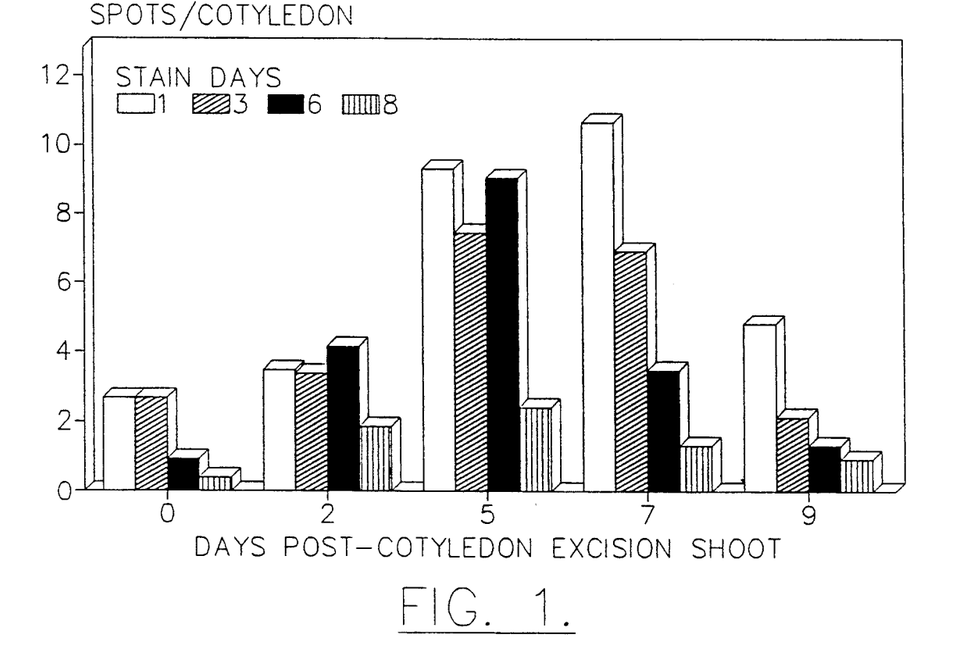
FIG. 1 graphically illustrates beta-glucuronidase (GUS) expression in *Pinus taeda* cotyledons transformed as described herein, with cotyledons bombarded on day 0, 2, 5, 7, and 9 after excision from their embryo after five days of germination in hydrogen peroxide, and with the transformed cotyledons stained to detect GUS expression on days 1, 3, 6, and 8 after bombardment.

FIG. 1 shows the data obtained from this procedure. The y-axis shows the number of blue spots counted per cotyledon, and the x-axis shows the days of induction before bombardment (or "shooting"). Each cluster of bars on the histogram represents all of the time points for staining for a given bombardment day. It will be seen that GUS expression is increased when bombardment is carried out between about days 2 to 9 after excision, and is most increased when bombardment is carried out between about days 5 to 7 after excision.

Figure 2:
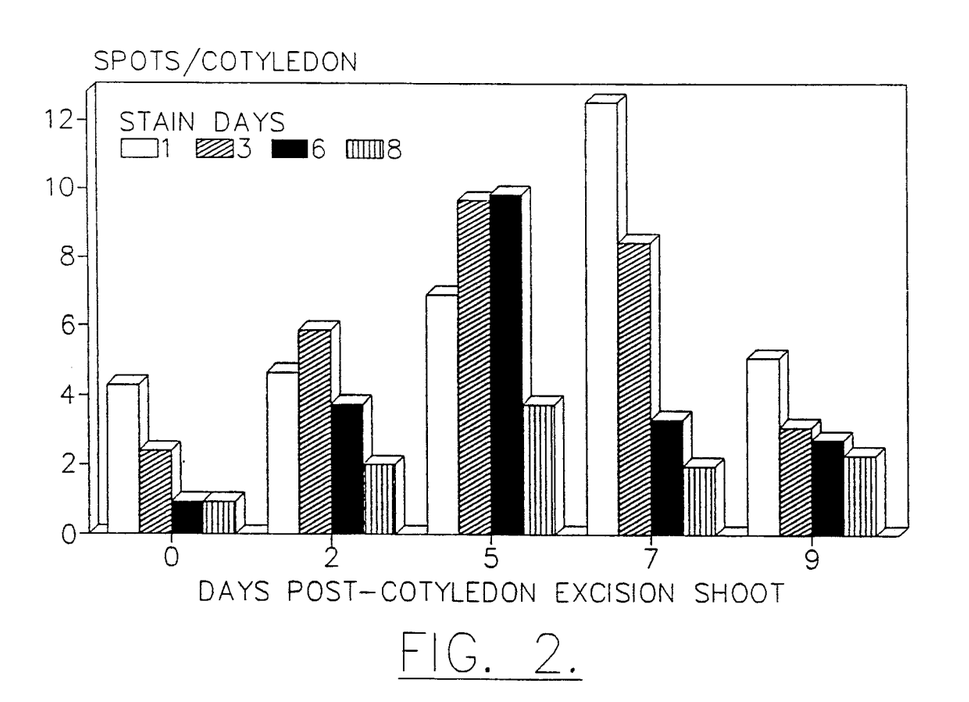
FIG. 2 graphically illustrates the results of essentially the same experiment as illustrated in FIG. 1, except that the cotyledons in this experiment were bombarded twice.
Figure 3:
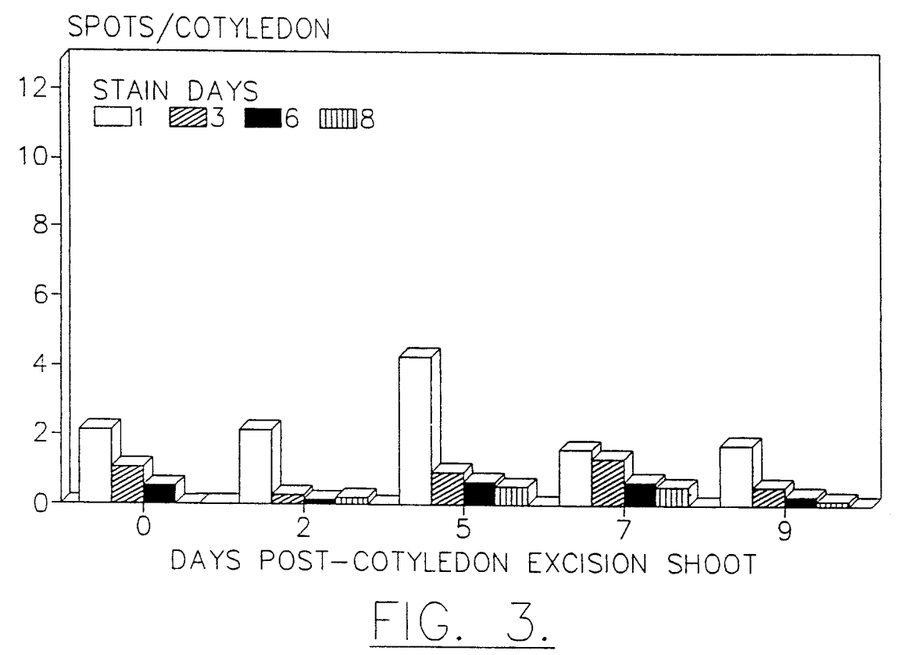
FIG. 3 graphically illustrates the results of a replicate of the experiment illustrated in FIG. 1.
Figure 4:
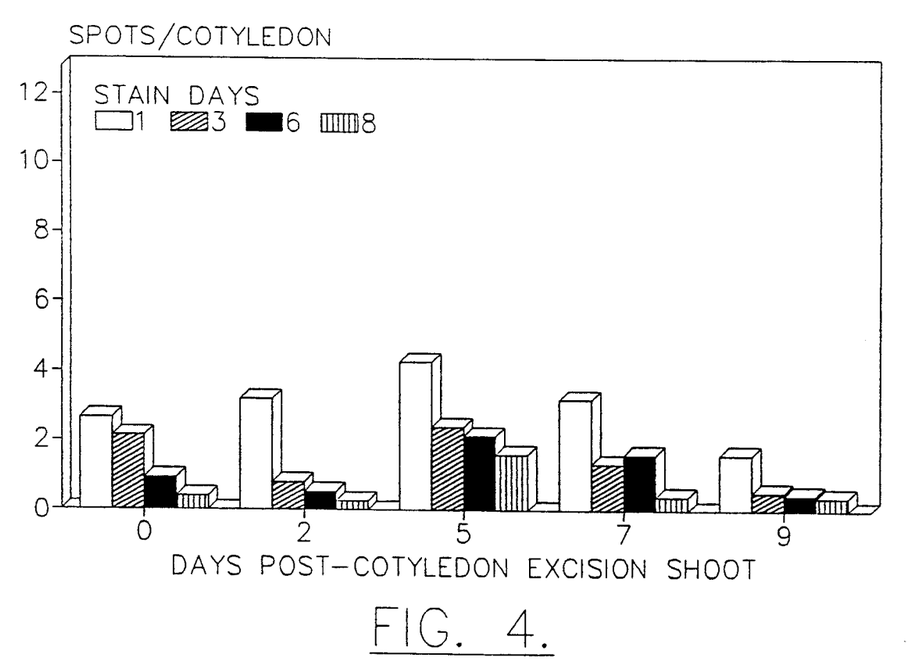
FIG. 4 graphically illustrates the results of a replicate of the experiment illustrated in FIG. 2.

FIG. 2 is data from an experiment carried out the same as the experiment for which results are given in FIG. 1, except that the cotyledons were bombarded twice. Two bombardments consistently give slightly higher average values than single bombardments. FIG. 3 displays data from a replicate experiment of that shown in FIG. 1, and FIG. 4 displays data from a replicate experiment of that shown in FIG. 2.

EXAMPLE 9

Determining the Effect of Time of Bombardment on GUS Expression in *Pinus radiata*

Figure 5:
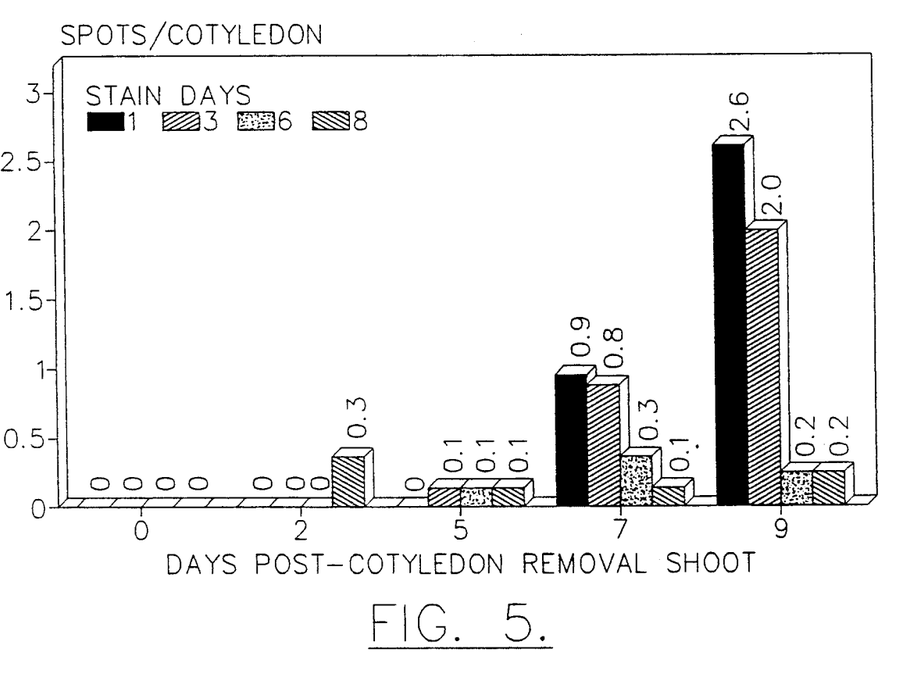
FIG. 5 graphically illustrates the results of an experiment similar to that illustrated by FIG. 1, except that *Pinus radiata* seed was employed.

This experiment was carried out in essentially the same manner as the experiment described in Example 8 above, except that *Pinus radiata* seed was used, and the seed was germinated for only one day. The cotyledons were bombarded once. Data from this experiment is shown in FIG. 5. Note the enhanced expression of GUS activity for tissue bombarded on about day 2 or later, and particularly for tissue bombarded on about day 7 or later.

The foregoing examples are illustrative of the present invention, and are not to be taken as restrictive thereof.

The invention is defined by the following claims, with equivalents of the claims to be included therein.

We claim:

1. A method of transforming conifers with a DNA construct comprising an expression cassette, which construct comprises, in the 5' to 3' direction, a transcription initiation region and a peptide coding region positioned downstream from said transcription initiation region and under the transcriptional regulation thereof, said method comprising the steps of
   (a) providing a plant tissue target, said plant tissue target comprised of conifer tissue selected from the Pinaceae family, the cells of said conifer tissue including cell walls; and
   (b) propelling said DNA construct at said plant tissue target at a velocity sufficient to pierce said cell walls and deposit said DNA construct within a cell of said tissue target to thereby provide a transformed plant tissue; wherein said DNA construct is carried by a microprojectile, and wherein said DNA construct is propelled at said plant tissue target by propelling said microprojectile at said plant tissue target; and then
   (c) generating shoots from said transformed plant tissue.

2. A method according to claim 1, wherein said conifer tissue is selected from the class consisting of genus Pseudotsuga, genus Tsuga, genus Picea, genus Sequoia, genus Abies, genus Thuja, genus Libocedrus, genus Chamaecyparis, and genus Laryx.

3. A method according to claim 1, wherein said conifer tissue is Pinus tissue.

4. A method according to claim 1, wherein said conifer tissue is Pinus tissue selected from the class consisting of loblolly pine (*Pinus taeda*), slash pine (*Pinus elliotii*), longleaf pine (*Pinus palustris*), shortleaf pine (*Pinus echinata*), ponderosa pine (*Pinus ponderosa*), red pine (*Pinus resinosa*), jack pine (*Pinus banksiana*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*), and Virginia pine (*Pinus virginiana*) tissue.

5. A method according to claim 1, wherein said conifer tissue is *Pinus taeda* tissue.

6. A method according to claim 1, wherein said conifer tissue is selected from the class consisting of meristematic tissue and tissue capable of induction into meristematic tissue.

7. A method according to claim 1, wherein said DNA construct comprises a plasmid.

8. A method according to claim 1, wherein said DNA construct is subject to the proviso that T-DNA borders are excluded therefrom.

9. A method according to claim 1, wherein said region which codes for a peptide codes for the production of beta-glucuronidase.

10. A method according to claim 1, wherein said microprojectile comprises a metallic particle.

11. A method according to claim 1, wherein said microprojectile comprises a metallic particle having a diameter of from about one-half micrometer to about three micrometers.

12. A method according to claim 1, wherein a plurality of said microprojectiles are provided, each of said microprojectiles having said DNA construct immobilized thereon, and each of said microprojectiles being propelled at said plant tissue target.

13. A method according to claim 1, further comprising the step of generating roots from said transformed plant tissue.

14. A method of transforming conifers with a DNA construct comprising an expression cassette, which construct comprises, in the 5' to 3' direction, a transcription initiation region and a peptide coding region positioned downstream from said transcription initiation region and under the transcriptional regulation thereof, said method comprising the steps of
   (a) providing a plant tissue target, said plant tissue target comprising Pinus tissue selected from the class consisting of meristematic tissue and tissue capable of induction into meristematic tissue, the cells of said Pinus tissue including cell walls; and
   (b) propelling said DNA construct at said plant tissue target at a velocity sufficient to pierce said cell walls and deposit said DNA construct within a cell of said tissue target to thereby provide a transformed plant tissue, wherein said DNA construct is carried by a microprojectile, and wherein said DNA construct is propelled at said plant tissue target by propelling said microprojectile at said plant tissue target; and then
   (c) generating shoots from said transformed plant tissue.

15. A method according to claim 14, wherein said Pinus meristematic tissue is selected from the class consisting of loblolly pine (*Pinus taeda*), slash pine (*Pinus elliotii*), longleaf pine (*Pinus palustris*), shortleaf pine (*Pinus echinata*), ponderosa pine (*Pinus ponderosa*), red pine (*Pinus resinosa*), jack pine (*Pinus banksiana*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*), and Virginia pine (*Pinus virginiana*) meristematic tissue.

16. A method according to claim 14, wherein said Pinus tissue is *Pinus taeda* tissue.

17. A method according to claim 14, wherein said Pinus tissue is selected from the class consisting of cotyledon tissue and hypocotyl tissue, and which tissue has been raised on shoot induction medium for a time at least sufficient to induce the subsequent formation of meristematic tissue thereon, and wherein said DNA construct is propelled at said target tissue before said target tissue is transferred to a growth medium for the production of rootable shoots.

18. A method according to claim 14, wherein said DNA construct comprises a plasmid.

19. A method according to claim 14, wherein said DNA construct is subject to the proviso that T-DNA borders are excluded therefrom.

20. A method according to claim 14, wherein said region which codes for a peptide codes for the production of beta-glucuronidase.

21. A method according to claim 14, wherein said microprojectile comprises a metallic particle.

22. A method according to claim 14, wherein said microprojectile comprises a metallic particle having a diameter of from about one to about three micrometers.

23. A method according to claim 14, wherein a plurality of said microprojectiles are provided, each of said microprojectiles having said DNA construct immobilized thereon, and each of said microprojectiles being propelled at said plant tissue target.

24. A method according to claim 1, wherein said plant tissue target is selected from the group consisting of pollen, embryos, cotyledons, hypocotyls, megagametophytes, callus, stems, needles, needle fascicles, existing meristematic tissue, and induced meristem tissue.

25. A method according to claim 1, wherein said plant tissue target is selected from the group consisting of embryos and cotyledons.

* * * * *

UNITED STATES PATENT AND TRADEMARK OFFICE
CERTIFICATE OF CORRECTION

PATENT NO.  : 5,122,466
DATED       : June 16, 1992
INVENTOR(S) : Anne-Marie Stomp; Arthur K. Weissinger; Ronald R. Sederoff It is certified that error appears in the above-identified patent and that said Letters Patent is hereby corrected as shown below:

Column 3, line 50, please change "Acrobacterium" to --Agrobacterium--.

Column 10, Table 1, Sub-heading Medium Concentration (mM), the third line, please change "0.001" to --0.0001--.

Signed and Sealed this

Thirteenth Day of July, 1993

Attest:

MICHAEL K. KIRK

Attesting Officer

Acting Commissioner of Patents and Trademarks